United States Patent [19]

Simon et al.

[11] 4,444,476
[45] Apr. 24, 1984

[54] OBJECTIVE REFRACTOMETERS

[75] Inventors: Jacques F. Simon, Paris; Didier R. Bruneau, Palaiseau; Joël E. Corno, Angervillers, all of France

[73] Assignee: Fiat Francais, France

[21] Appl. No.: 280,216

[22] Filed: Jul. 6, 1981

[30] Foreign Application Priority Data

Jul. 31, 1980 [FR] France .............................. 80 16001

[51] Int. Cl.³ .............................................. A61B 3/10
[52] U.S. Cl. ..................................... 351/211; 351/221
[58] Field of Search ................................ 351/211, 221

[56] References Cited

U.S. PATENT DOCUMENTS 3,874,774  4/1975  Humphrey ........................ 351/211
3,927,933  12/1975  Humphrey ........................ 351/211

Primary Examiner—John K. Corbin
Assistant Examiner—P. M. Dzierzynski
Attorney, Agent, or Firm—Parkhurst & Oliff

[57] ABSTRACT

An objective refractometer which enables a doctor to visually conduct optical pointings by projecting onto the retina of a patient an image coming from at least one point light source. The image is projected along an image projection path and observed through an observation path. A stand supporting the refractometer has stationary objective lenses mounted thereon while a movable unit carries an eyepiece and other apparatus which augment the projection and observation paths. An electronic control means comprising a microprocessor is operatively associated with a linear displacement detector, which detects movement of said movable unit relative to the stand, and an angular displacement detector, which detects angular rotation of test patterns on the optical axes of said projection and/or observation paths, as well as apparatus for operator controlled transmission of information derived from the detectors.

9 Claims, 13 Drawing Figures

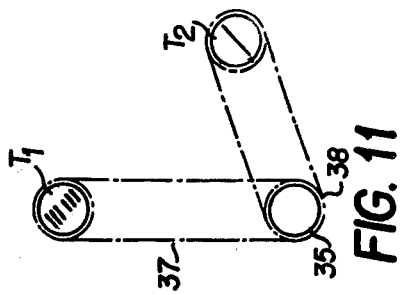
FIG. 11
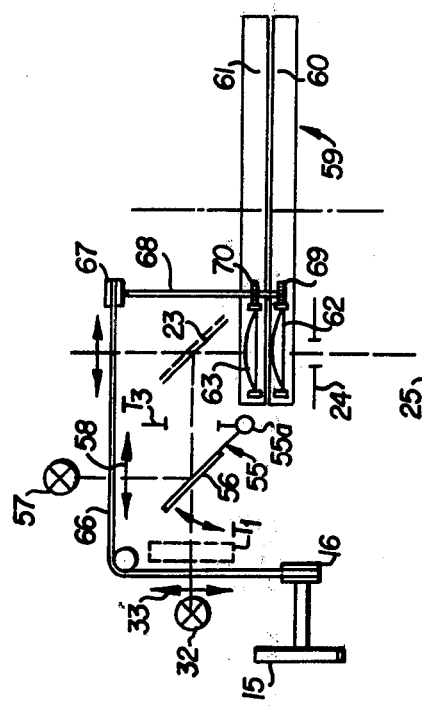
FIG. 12
FIG. 10
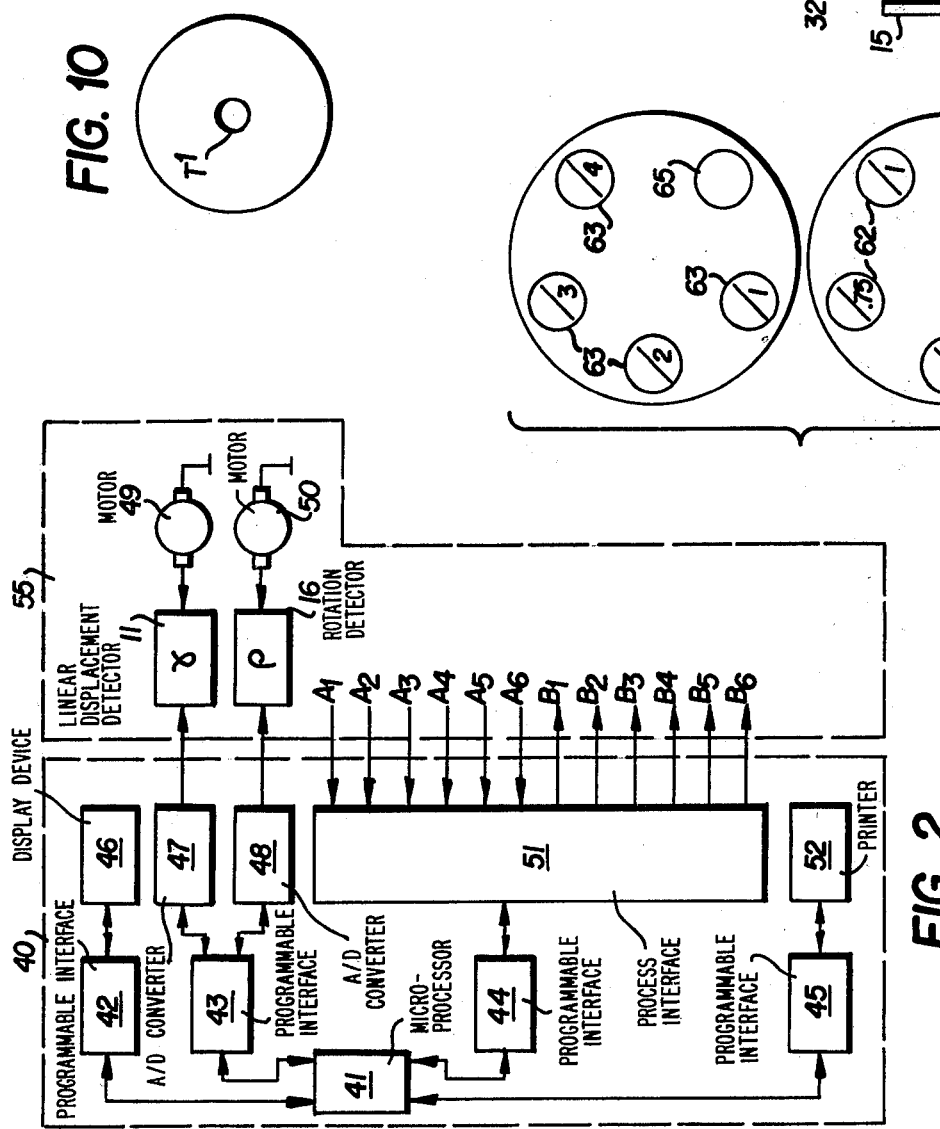
FIG. 13
FIG. 2

OBJECTIVE REFRACTOMETERS

The present invention concerns objective refractometers and refers more particularly to such a refractometer assisted by a microprocessor.

Any instrument which permits the practitioner to determine the ametropia of the patient by examination of a test pattern projected on his retina is known as an objective optometer or objective refractometer.

Among instruments of this type we will examine essentially apparatus in which the information is acquired visually by the practitioner.

Some of these apparatus make it possible to proceed with the examination of test patterns projected onto the retina of the patient.

The pointing is obtained when the test pattern projected across the eye of the patient appears sharp to the practitioner at the retina of the patient.

Various apparatus have been developed in accordance with this principle.

Among these apparatus mention may be made of the RODENSTOCK ocular refractometer, the THORNERBUSCH refractometer and the ARNULF refractometer.

The use of objective refractometers has been described in an article by G. SOBREPERE which forms part of the transactions the Hotel-Dieu Ophthalmological Clinic published by the H. FAURE d'ANNONAY Laboratories in 1970.

There is a second type of refractometer which employs the SCHEINER principle and consists of assuring the projection through two distinct zones of the pupil of a linear test pattern orthogonal to the two pupillary zones, the image of which is located in the vicinity of the retina.

If the image is located in the plane of the retina, the image of a single luminous slit is observed.

If the image is located in front of or behind the retina, two distinct luminous slits are observed.

The doubling of these images is directly proportional to the lack of convergence of the eye in question.

The FINCHAM refractometer is developed in accordance with the said principle.

For several years there have been automatic refractometers which require the presence of a medical assistant only to position the patient with respect to the instrument.

This operation having been effected, the instrument directly effects the optical targeting by photoelectric measurement and prints on a ticket the information corresponding to the characteristics of the corrective lenses to be prescribed for the patient.

One apparatus of this type has been described in French Pat. No. 2 228 461. In accordance with the technique described in that patent, the image of a dioptric rule is projected onto the retina of the patient via an optical system. The ophthalmoscopic image is analyzed after a double passage through the eye, by a dioptric rule of pitch identical to the object dioptric rule and a photodetector delivers an electric signal which is proportional to the contrast of the image. This signal serves to feed a motor which modifies the position of the optical system so as to obtain the maximum signal for the optimum focusing.

The exploration of astigmatism is assured by simultaneously turning the object-dioptric rule and the analysis-dioptric rule along six meridians.

The source of light used is a source of infrared rays. The measurement on an eye takes 30 seconds.

This apparatus is, in fact, a photoelectric transposition of refractometers which operate by visual examination of a test pattern projected on the retina of a patient.

Another automatic apparatus is described in French Pat. No. 2 204 805.

This apparatus employs the SCHEINER principle.

In accordance with this principle, a beam of light is imparted a linear movement. After reflection on the retina of the eye of a patient, the beam of light falls on a fourquadrant receptor. The combination of the signals coming from each sensitive field gives information as to the spherical power and information as to the direction of the axis of the cylinder. The signals obtained act on two motors.

The first motor turns the apparatus axially so that the signals corresponding to the measurement of the axis of the cylinder cancel each other out.

The second motor displaces the detector along the optical axis of the system so as to bring it to focus.

It will be noted that after the positioning of the subject the centering is assured automatically.

There are therefore two large categories of refractometers:

The visual objective refractometers which are simple apparatus and which require the intervention of the doctor.

The automatic objective refractometers which require only paramedical personnel employing receivers, possibly a minicomputer or analog electronic circuits, and which directly deliver the information relating to the correction to be made for the eye of the patient.

These last-mentioned apparatus emply infrared light, which has the advantage for the patient that it is not visible, but the disadvantage of which is that it produces, due to the chromatism of the eye, a measurement which does not correspond to the normal use of the eye. The result is that the chromatic correction is difficult to effect on basis of these measurements, since its change with the different patients is unknown.

Furthermore, while the visual objective refractometers require the intervention of the doctor, who must in particular effect a certain number of manipulations and difficult calculations, the automatic objective refractometers have the opposite drawback in the sense that their operation cannot be influenced in any way by the doctor, who is therefore robbed of any initiative which he could take as a function of a preliminary diagnosis which he made on his patient.

The invention is directed at overcoming the drawbacks of both the visual refractometers and the automatic refractometers by creating an apparatus in which the practitioner can effect the pointing and directly observe the quality of the retinal image while the measurement proper is effected by means which assure the rapid determination of the information and its processing and which directly provide information relating to the correction to be made on the eye examined.

Its object therefore is a method to determine the ametropia of the eye of a patient by means of an objective refractometer which consists in displacing at least one test pattern with respect to the eye of the patient along the direction of the optical axis thereof, observing the image of this test pattern formed on the retina of the eye and effecting an optical pointing on the sharp image of the test pattern when the latter reaches the far point of the eye, the shape of said image and the value of the far point constituting the information necessary for the determination of the ametropia, characterized by the fact that after each determination of a far point, the test pattern is automatically returned to initialization position which is a hypermetropic position for the majority of patients.

When the shape of the image of the test pattern at the far point discloses such astigmatism, the method advantageously consists in orienting the test pattern along the direction of the astigmatism and it is characterized by causing, before the automatic return of the test pattern to its initialization position, a rotation of the said test pattern through 90° with respect to the said orientation and continuing the displacement of the test pattern along the direction of the optical axis of the eye up to of the far point of the new orientation.

In accordance with another characteristic, the process consists furthermore in verifying the correction to be made for the ametropia revealed by inserting into the real space of the eye or preferably into a conjugate space thereof at least one corrective lens and orienting the said correction lens in synchronism with the orientation of the test pattern.

Another object of the invention is an objective refractometer intended to use the process described above in order to permit the doctor visually to effect the optical sightings by projecting onto the retina of the patient the image of at least one point light source, the said refractometer having a stand bearing fixed objectives and means forming part of a lower image projection path and of an upper image observation path, as well as a movable unit bearing an eyepiece and comprising means supplementing said upper and lower paths, characterized by the fact that it comprises furthermore electronic control means comprising a microprocessor associated with a means for detecting linear displacements of the movable portion with respect to the stand and a means for detecting angular displacements of the test patterns around optical axes of the said lower and/or upper paths, as well as means for the transmission, under the control of the doctor, of the information given by the said detector means.

Other characteristics of the invention will become evident during the course of the following description, read with reference to the accompanying drawings, given solely by way of example, in which:

FIG. 2 is a synoptic diagram of the electronic and data unit intended to control the apparatus of the invention;

FIG. 10 is a view of the test pattern seen in the direction of the arrow G of FIG. 9;

FIG. 11 is a view of the appearance of the test patterns $T_1$ and $T_2$ in the direction of the arrow the affow F in FIG. 9;

FIG. 12 is a view corresponding to those of FIGS. 5, 8 and 9 showing a correction verification device incorporated in the apparatus of the invention, and FIG. 13 is a front view of the two elements of the refractor of FIG. 10 arranged side by side.

Figure 1:
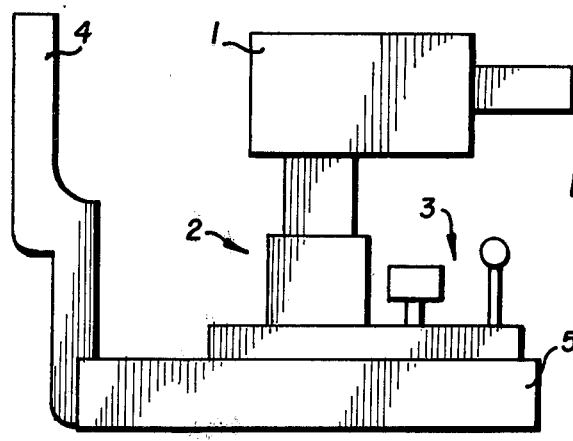
FIG. 1 is a diagrammatic view of the optical and mechanical unit of the refractometer of the invention.

The apparatus of the invention, which is shown diagrammatically in FIG. 1 comprises essentially a main part 1 of the refractometer, mounted on a support 2 with three degrees of freedom provided with suitable control means 3 intended to position the apparatus with respect to the eye of the patient.

The apparatus furthermore has a forehead rest 4 which, together with the support 2, is fastened on a base 5.

This assembly constitutes the refractometer proper and rests on a table.

Figure 3:
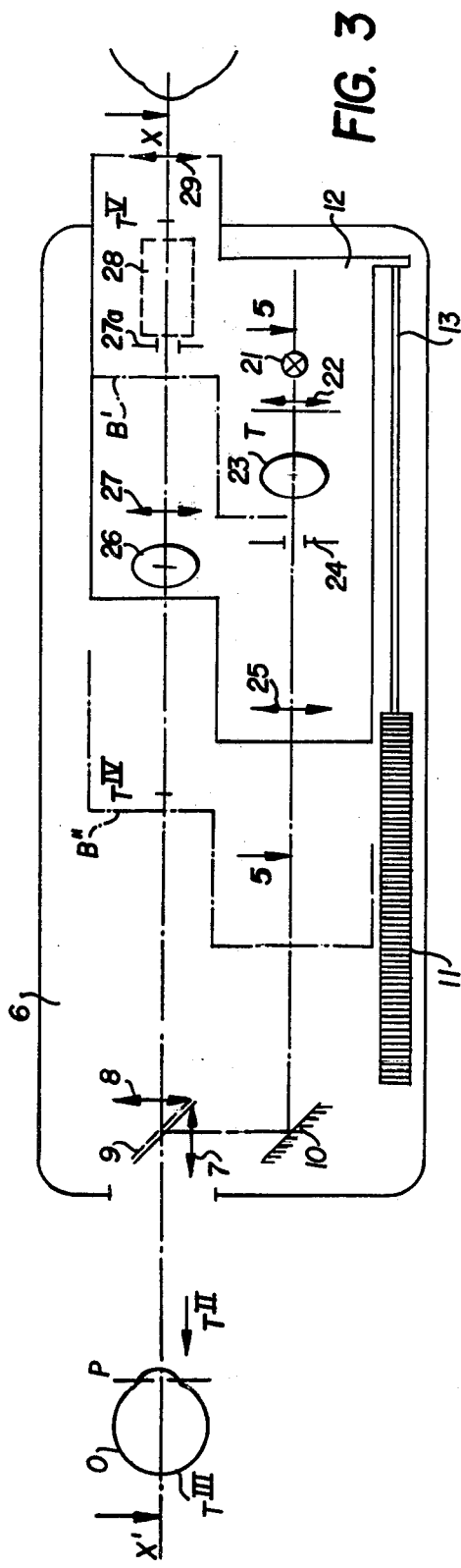
FIG. 3 is a view in elevation in cross-section of the main part of the refractometer of FIG. 1.
Figure 4:
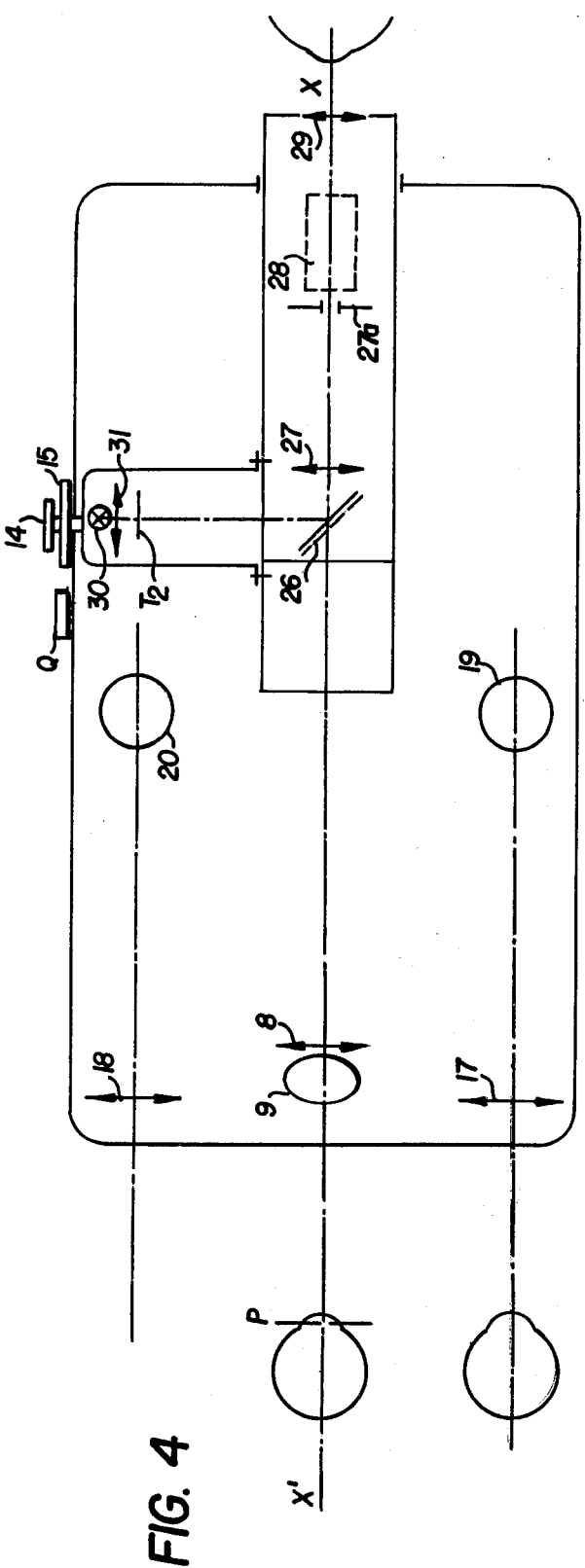
FIG. 4 is a top sectional view of the part of the apparatus shown in FIG. 3, along the line X—X' of FIG. 3.

The main part 1 of the refractometer is shown in greater detail in FIGS. 3 and 4.

The unit 1 comprises a stand 6, identical objectives 7, 8 with telecentric pupil the optical axes of which are perpendicular, a beam splitter 9 consisting of a semi-transparent plate arranged at the intersection of the optical axes of the objectives 7 and 8, a flat mirror 10 located on the optical axis of the objective 7 and intended to reflect the light beams which traverse said objective in a direction parallel to the optical axis of the objective 8. The assembly furthermore comprises a linear displacement detector 11, consisting, for instance, of a potentiometer whose wiper is mechanically connected to a movable unit 12 via a rod 13.

As can be noted from FIG. 4, the detector 11 is actuated by a control knob 14 which acts on a pinion cooperating with a rack connected to the movable part 12 which has not been shown in the drawings.

The apparatus furthermore comprises a control knob 15 intended to assure the rotation of a rotation detector 16 (FIG. 8) and two test patterns T and $T_1$ located in the movable part 12. It also comprises collimators 17 and 18 associated with illuminating devices 19 and 20 making it possible to obtain a uniform circular field.

The movable unit 12 is displaceable in translation on the stand 6 between two extreme positions B' and B".

As can be noted from FIG. 3, it has a lower path and an upper path.

On the lower path, which is intended to assure the projecting of the image there is a source of light 21 which may be a tungsten filament lamp or an iodine or arc lamp or else a gas or solid laser, said source being intended to illuminate, via a condenser 22, holes T whose diameter is less than 50 μm and which constitute perfectly defined auxiliary sources.

On the lower path there is also present a beam mixer 23, an entrance pupil 24 for the system, a vehicle lens 25 intended to assure the transport of the images T, the mirror 10, the objective 7 and the beam splitter 9, these last three elements being rigidly connected to the stand 6.

The upper path, intended to assure the observation of the image comprises the splitter 9 which operates by transmission and the objective 8 which are rigidly connected to the stand 6, the objective 8 being identical to the objective 7, a mixer 26, a vehicle 27, a retractable vehicle 28 and an eyepiece 29.

In FIG. 4 there can again be noted the elements 26, 27, 28 and 29. There is furthermore shown the action of the beam mixer 26 which makes it possible to superimpose on the main beam a graticule T2 which is illuminated by an associated source 30 and condenser 31. The graticule T2 constitutes an accommodation reference and permits the doctor by acting on the eyepiece 29 to adjust the image of the graticule T2 to his convenience.

In FIG. 4 there can also be again noted the lateral collimators 17 and 18 associated with the illuminating devices 19 and 20. In this figure there has been shown a measurement relating to the left eye of a patient, so that the illuminating device 19 is lit while the illuminating device 20 is extinguished.

Figure 5:
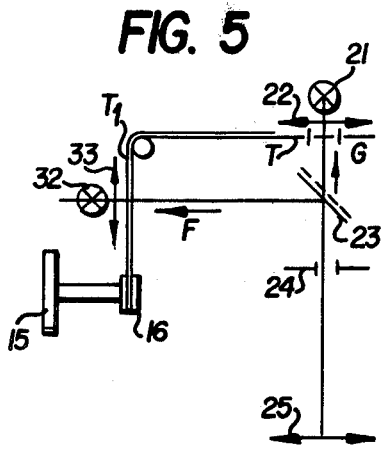
FIG. 5 is a section along the line 5—5 of FIG. 3.

In FIG. 5 the elements 21, 22, T, 23 and 24 can again be noted. There can be seen in this figure the action of the beam mixer 23 which makes it possible to superimpose upon the holes T the test patterns T1 which are illuminated by an auxiliary source 32 with which a condenser 33 is associated. FIG. 5 also shows that the test pattern T1 is fixed in rotation to the angular detector 16 which may be actuated by the control knob 15.

Figure 6:
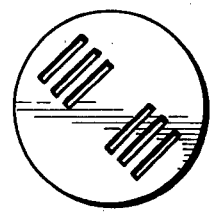
FIGS. 6 and 7 are projections of two aspects of the linear test patterns obtained with the arrangement of FIG. 5.

The appearance in projection of the test pattern T1 is shown in FIG. 6.

Figure 7:
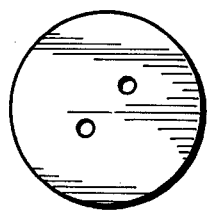

The appearance of the test pattern T in projection along the line G is shown in FIG. 7.

Figure 8:
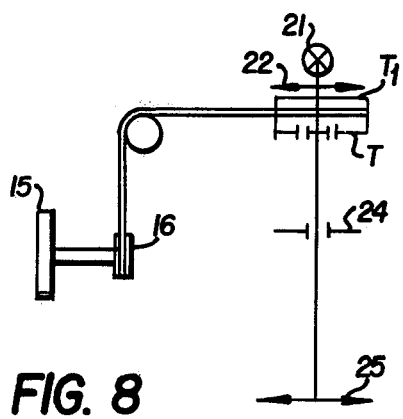
FIG. 8 is a simplified variant of the arrangement of FIG. 5.

In FIG. 8 a simplified variant of the arrangement of FIG. 5 is shown. In this figure there can again be noted the elements 21, 22, T, T1, 24, 25, the angular detector 16 and its control knob 15. On the other hand, the elements 23, 32 and 33 of FIG. 5 are no longer present in the embodiment shown in FIG. 8.

Such a variant can be developed by replacing the test pattern T constituted in the embodiment of FIG. 5 by an opaque support pierced with holes, by a support of weak transmission and formed of holes of high transmission. This embodiment is possible by employing the techniques of vacuum metal spraying of a glass plate.

The arrangement of FIG. 8 is advantageous in that it makes it possible to eliminate an auxiliary source and a beam mixer.

Figure 9:
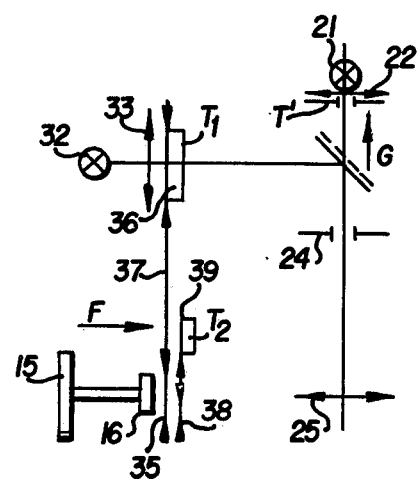
FIG. 9 is a view of another variant of the arrangement of FIG. 5 in which a test pattern consisting of a single hole located on the optical axis of the apparatus is used.

It is also possible to replace the test pattern T formed of two or more aligned holes by a test pattern T' formed of a single hole located on the optical axis of the lower path. Of course, in such case it is not necessary to turn the test pattern T' since such a rotation would not produce any effect. Such an arrangement is shown in FIG. 9 in which the elements corresponding to the embodiment of FIG. 5 are designated by the same reference numbers. The control knob 15 for the angular detector 16 also assures the rotation of the test pattern T1 via two pulleys 35 and 36 and a belt 37. However, via a pulley 38, keyed on the axis of the control knob 15, and a pulley 39 it also assures the rotation of the test pattern T2 of the upper path consisting of a directional reference mark illuminated by the source 30 (FIG. 4).

The appearance of the test pattern T' is shown in FIG. 10 while that of the test patterns T1 and T2, seen coupled in rotation via pulleys 35 and 38 is shown in FIG. 11.

The electronic and data unit of the refractometer of the invention is shown in the form of a synoptic diagram in FIG. 2. This unit is divided into two parts, namely:

A first part 40 comprises all the electronic elements corresponding to the processing of the signal. It comprises a microprocessor 41 which, in the present example, is an M6800 microprocessor manufactured and sold by the MOTOROLA company.

The microprocessor is connected to four programmable interfaces 42 to 45. The interface 42 is connected to an electronic display device 46.

The interface 43 is connected to analog-digital converters 47 and 48 which in their turn are connected to the linear displacement detector 11 and the rotation detector $p16$. In the embodiment shown in FIG. 2, the detectors 11 and 16 are coupled to two drive motors 49 and 50 respectively.

The motor 49 is intended to drive the movable unit 12 towards an initialization position after the end of each measurement.

The motor 50 is intended to turn the test patterns T1 and T2 upon an astigmatism measurement.

The programmable interface 44 controls and receives the information of an interface 51 which processes six input data and delivers six output data. The input data are as follows:

A1 indicates that the refractometer is in adjusted position;

A2 indicates that the right eye (OD) or the left eye (OG) is being examined;

A3 indicates that an additional lens of a power equal to $-7$ diopters has been put in place;

A4 indicates that an additional lens of a power equal to $+7$ diopters has been put in place;

A5 indicates that the data input pushbutton Q has been pushed (FIG. 2);

A6 indicates that it is desired to print the results on the printer 52 which is connected to the programmable interface 45.

The outputs of the interface 51 are as follows:

B1 assures the placing in operation or stopping of the motor 49 which drives the movable unit 12 of FIG. 3 towards its initialization position which is a hyperoptic position of the patients;

B2 starts or stops the motor 50 which assures the driving in rotation of the test patterns T and T1 or of the test patterns T2 and T1 for an astigmatic patient depending on the arrangement adopted, as appears from FIGS. 5 and 9;

B3 assures the signalling by a signal lamp that an additional element of a power of $+7$ diopters has been put in place;

B4 indicates by means of a signal lamp that an additional element of a power of $-7$ diopters has been put in place;

B5 determines the direction of rotation of the motor which drives the movable unit 12;

B6 indicates the direction of rotation of the motor controlling the rotation of the test patterns T, T1 or T2, T1 depending on the arrangement adopted.

The electronic unit shown in FIG. 2 comprises a second part, indicated generally as 55 which comprises in addition to the linear and angular displacement detectors 11 and 16 and the motors 49 and 50 associated with them, all the actuating and signalling elements necessary for the processing of the inputs A1 to A6 of the interface 51 and the execution of the instructions corresponding to the outputs B1 to B6 of said interface.

The operation of the refractometer of the invention will first of all be described in the case of a measurement on a non-astigmatic eye.

It will be recalled that a non-astigmatic eye is an eye having symmetry of revolution around its optical axis. This eye may have a defect in power.

The positioning of the apparatus with respect to the head of the subject resting on the forehead rest 4 shown in FIG. 1 is effected by the doctor who looks into the eyepiece 29 of the refractometer, the vehicle 28 being put in place.

To this situation there corresponds the appearance of a signal at the input A1 of the interface 51 of the circuit of FIG. 2. This information is transmitted to the microprocessor 41 which has the effect of blocking the entire measurement process.

The only information taken into consideration is the information A2 relative to the eye examined and A3 and A4 relative to the power of the additional lenses. These two last-mentioned bits of information reach the practitioner in the form of output signals B3 and B4 which cause the lighting up of two signal lights, not shown. In the adjusted position corresponding to the presence of a signal on the input A1 of the interface 51, the lights $A_3$ or $A_4$ blink. This operation being effected, the vehicle 28 is retracted and the practitioner can effect the measurement of the spherical ametropia of the patient. The information A1 disappears from the corresponding input of the interface and this measurement is then effected in the following manner. The vehicle 25 of the lower path of the apparatus assures the optical transport of the auxiliary source T to the point $T^I$ located on the optical axis of the lower path. The objective 7, the mirror 10 and the splitter 9 assure the real or virtual projection of the source $T^I$ at a point $T^{II}$ which may occupy any position along the optical axis x—x' of the upper path of the apparatus, within a limited dioptric range. The different positions of $T^{II}$ are obtained by displacing the movable unit 12 with respect to the stand 6.

The doctor adjusts the control knob 14 shown in FIG. 4 in order to form the image $T^{III}$ of the point $T^{II}$ on the retina of the eye 0 of the patient. The objectives 7 and 8 being completely identical the image formation criterion is obtained, seeking to make its dimensions minimum through the eyepiece 29.

If the image $T^{III}$ reflected by the retina is in its plane, its image given by the optical system of the eye is found again at $T^{II}$. It is then taken up by the splitter 9 which acts by transmission and the objective 8 gives an image thereof which is formed at $T^{IV}$. The vehicle 27 at this point gives an image located at $T^V$ which is observed by the doctor due to the eyepiece 29.

The identical ophthalmoscopic objectives 7 and 8 may in certain cases be devices which present for the patient an image distance greater than their focal length.

The additional lenses of a power of ±7 diopters approximately can be placed either between the eye of the patient and the apparatus or within the instrument in the conjugate spaces of the plane P of the eye of the patient, that is to say in the vicinity of the pupil 24 of the lower path and of the pupil 27a of the upper path.

The measurements effected by the detectors 11 and 16 are transmitted at each moment to the microprocessor 41 via the interfaces 47 and 48. The microprocessor effects the calculation of a function $Y = -(Ax+B)/(Cx+D)$ in which x is the information delivered by the detector 11 while A, B, C, D are parameters related to the optical system used in the refractometer and are selected in such a manner that Y represents the value of the spherical correction to be placed at a given distance of 12 mm from the vertex of the cornea of the eye examined.

The microprocessor 41 also effects the calculation of the azimuth in degrees modulo 180° by means of the information delivered by the detector 16. The information as to dioptric power and azimuth is displayed in real time on the electronic display device 46. It will be noted that in this case the information delivered by the detector 16 is transmitted to the microprocessor but it is not processed by the latter since a non-astigmatic eye is concerned.

When the doctor has effected the painting, he pushes on the switch Q which sends information intended for the microprocessor 41 to the input A5.

The microprocessor sends the value Y of the spherical power which it has found to the display device 46.

Let us now examine the operation of the refractometer of the invention upon the measurement of an astigmatic eye.

The single pointing which in the preceding example gives the measure of the ametropia is replaced by two pointings obtained by adjustment of the knob 14 (FIG. 3) corresponding to the dioptric positions of the focal length and by two angular orientations obtained by action on the angular displacement knob 15, these orientations corresponding to the directions of the focal lengths.

Therefore a first sighting is effected by transferring the information coming from the detectors 11 and 16 to the microprocessor 41 by means of the push button Q. After processing, the value of the sphere appears on the electronic display device 46.

The second sighting is then effected by the doctor by means of the push button Q. The new information coming from the detectors 11 and 16 is again transmitted to the microprocessor which processes the entire group of four data and the new sphere value Y which corresponds to the second sighting; the value of the cylinder obtained by the difference of the two values Y obtained for each sighting as well as the angular orientation are displayed on the device 46.

After the first sighting, the motor 50 (FIG. 2) turns the knob 15 to which it is connected through an angle of 90° under the action of the signals appearing on the outputs B2 and B6 of the interface 51, which avoids the second angular sighting.

In all cases, whether the eye is non-astigmatic or astigmatic, the doctor can obtain the values of the sphere and of the cylinder and its angular orientation on a ticket delivered by the priner 52 for the right eye and the left eye. For this purpose it is sufficient to cause the appearance of a signal on the input A6 of the interface 51 by means, for instance, of a push-button switch.

After printing, the movable unit 12 is returned under the action of signals appearing on the outputs B1 and B5 of the interface 51 to a hypermetropic command position located at 5 diopters by means of the motor 49.

The originality of the refractometer which has just been described over the conventional refractometers resides in the following points:

A microprocessor is associated with the different displacement, illumination and measurement members of the apparatus;

Different measurement strategies are used depending on the programs recorded in the memories of the microprocessor, in particular with respect to the lens-eye correction;

There is automatic return to the hypermetropic position before another pointing;

The refraction and the azimuth of the focal lengths are displayed in real time in units of dioptric power and in degrees modulo 180°;

The results obtained for each eye are printed on a ticket;

A unidimensional test pattern is employed consisting of one or more thin black lines on a light background, as can be noted in particular from FIG. 6. This test pattern can turn in synchronism with the holes T or with the test pattern T2 of the upper path depending on the arrangement adopted, which enables the doctor to determine the orientation of the astigmatic focal distance; furthermore this test is shifted in hypermetropic position on the order of one diopter so as to realize the principle corresponding to the so-called fog method.

The microprocessor-assisted refractometer which has just been described lends itself well to a phase of verification of the correction to be made for the subject, which additional function can be integrated in the apparatus, as shown in FIGS. 12 and 13.

FIG. 12 is a view corresponding to FIGS. 5, 8 and 9 so that identical reference numbers have been assigned to the corresponding elements of these figures. However, the apparatus of FIG. 12 furthermore has a device for verification of the correction to be made in the eye whose ametropia has been determined.

This device comprises a retractable unit placed on the path of the light given off by the source 32 which illuminates the test pattern T1.

The assembly 55 is formed of a flat mirror 56 and of a test pattern T3 bearing an optotype which is rigidly connected with the said mirror and arranged with respect to it in such a manner as to be illuminated by the light from a source consisting of a lamp 57 and a condenser 58 which are analogous to the lamp 32 and the condenser 33 but are arranged in such a manner as to be able to illuminate the test pattern T3 via the mirror 56 when the latter masks the light coming from the lamp 32. The assembly 55 is mounted for rotation around a pin 55a.

The verification device furthermore comprises a refractor 59 arranged in the conjugate space of the eye, between the pupil 24 and the beam mixer 23.

This refractor is formed in known manner by two coaxial barrels 60, 61 mounted for rotation around an axis parallel to the optical axis of the assembly formed of the mixer 23, the pupil 24 and the vehicle lens 25.

Each barrel bears a series of cylindrical lenses 62, 63 of powers ranging from 0.25 to 1 diopter for the barrel 60 and from 1 to 4 diopters for the barrel 61.

Each barrel furthermore has a hole without lens 64, 65.

Finally the device comprises mechanical means for angular displacement of the lenses 62 and 63 in synchronism with the test pattern T1, these means being formed by a belt 66 driven by the pulley 16 which is connected to the knob 15, and passing over a second pulley 67 which is rigidly fastened on a shaft 68 bearing at its end pinions 69, 70 which mesh with internally toothed rings, not shown, forming part of the mounts of the corresponding lenses 62, 63.

The spherical correction is assured by the displacement of the movable unit 12 with respect to the stand 6, and the correction of the astigmatism is assured by the positioning of one or two cylindrical lenses 62, 63 in the conjugate space of the eye of the patient, that is to say within the apparatus in the vicinity of the diaphragm 24, as shown in FIG. 12. In this case, the apparatus is maintained in the position of the last pointing, and the dioptric value of the astigmatic correction delivered by the measurement is displayed on a drum (not shown). The action of this drum consists in placing the corrective cylindrical lens or lenses between the diaphragm 24 and the mixer 23. This lens is mechanically preadjusted in orientation as a result of the linear angular connection between the orientation of the test patterns (T1-T) or (T2-T1) and the orientation of the corrective cylindrical lens.

The refractor formed of cylindrical lenses such as the refractor 59 is used in subjective optometry.

During the course of the same operating sequence, the source 21 (FIG. 5 or 9) is extinguished and the test pattern T1 is replaced by a test pattern T3 consisting of the microscopic reduction of an optotype table.

We claim:

1. An objective refractometer which permits a practitioner visually to effect optical pointings by projecting onto the retina of a patient the image of at least one point light source, said refractometer comprising a stand bearing stationary objectives and means forming part of a an image projection path and means forming part of an image observation path as well as a movable unit bearing an eyepiece and comprising means supplementing said image projection and observation paths, said refractometer further comprising test patterns for image projection and electronic control means comprising a microprocessor (41) associated with a detector (11) of linear displacements of the movable part (12) with respect to the stand (6) and a detector (16) of angular displacements of at least one of said test patterns around optical axes of the said image projection path as well as means (43, 47, 48) for transmission, under the control of a practitioner, of the information derived from said detectors whereby said image is projected onto an eye and a pointing is effected whereupon the information from said indicators is transmitted to said microprocessor.

2. The objective refractometer of claim 1, wherein said microprocessor (41) is operatively connected to said linear displacement detector (11) and angular displacement detector (16) by said transmission means, said transmission means comprising a first programmable interface circuit (43) and an analog-digital converter (47, 48).

3. The objective refractometer of claim 1 or 2, wherein said microprocessor (41) is operatively connected by a second programmable interface circuit (42) to a digital display device (46).

4. The objective refractometer of claim 1 or 2, wherein said microprocessor (41) is operatively connected to a printer (52) by a third programmable interface circuit (45).

5. The objective refractometer of claim 2, further comprising a data interface circuit (51) for the processing of information derived from manipulations made by a practitioner on the refractometer, said data interface circuit capable of producing control or operation signals corresponding to the manipulations made by the practitioner.

6. The objective refractometer of claim 5, further comprising means (49) driven by the microprocessor (41) for returning the movable unit (12) automatically to an initial position which is a hyperopic position for the majority of patients, said return means (50) comprising an electric motor operatively associated with said linear displacement detector (11) which is controlled by the microprocessor (41) through the data interface circuit (51), the first programmable interface circuit (43) and analog-digital converter (47).

7. The objective refractometer of claim 5, for examination of an astigmatic eye, further comprising means (50) for rotating at least one of the test patterns through an angle of 90° with respect to the eye of a patient, said rotating means (50) comprising an electric motor associated with the angular displacement detector (16) and controlled by the microprocessor (41) through the data interface circuit (51), the first programmable interface (43) and the analog-digital converter (48).

8. A refractometer which enables the operator to visually observe the sighting of the projection of at least one optical image onto the retina of an eye while electronically processing the data attained thereby, comprising:
   a stationary base,
   first optical means for projecting an image onto the retina,
   second optical means for observing the image on the retina,
   said first optical means having a portion which is movable to various positions relative to said base to change the nature of said image on said retina in order to determine the capabilities of the eye,
   said second optical means enabling the operator by viewing therethrough to ascertain when a desired projection of said image is attained,
   means for detecting the location of said first optical means relative to said base,
   means for electronically processing information operatively connected to said detecting means, said means for electronically processing information comprising a microprocessor,
   a data interface circuit coupled to process information derived from manipulations made by a practitioner on the refractometer, said data interface circuit capable of producing control signals corresponding to the manipulations made by the practitioner, and
   means responsive to said microprocessor for returning said movable portion automatically to an initial position which is a hyperopic position for a majority of eye patients, said return means comprising an electric motor operatively coupled to said means for detecting and coupled for control by said microprocessor through said data interface circuit.

9. A refractometer which enables the operator to visually observe the sighting of the projection of at least one optical image onto the retina of an eye while electronically processing the data attained thereby, comprising:
   a stationary base,
   first optical means for projecting an image onto the retina,
   second optical means for observing the image on the retina,
   said first optical means having a portion which is movable to various positions relative to said base to change the nature of said image on said retina in order to determine the capabilities of the eye,
   said second optical means enabling the operator by viewing therethrough to ascertain when a desired projection of said image is attained,
   means for detecting the location of said first optical means relative to said base, said means for electronically processing information comprising a microprocessor,
   a data interface circuit coupled to process information derived from manipulations made by a practitioner on the refractometer, said data interface circuit capable of producing control signals corresponding to the manipulations made by the practitioner,
   means responsive to said microprocessor for returning said movable portion automatically to an initial position which is a hyperopic position for a majority of eye patients, said return means comprising an electric motor operatively coupled to said means for detecting and coupled for control by said microprocessor through said data interface circuit,
   means for providing a test pattern for projection as an image onto said retina,
   means for rotating said test pattern through an angle of 90° with respect to the eye of a patient,
   means for detecting the angular displacements of said test pattern around optical axes of said image projection,
   said rotating means comprising an electric motor associated with said means for detecting angular displacement and coupled for control by said microprocessor through said data interface circuit.

* * * * *